United States Patent
Koverech et al.

(10) Patent No.: US 8,158,679 B2
(45) Date of Patent: Apr. 17, 2012

(54) USE OF L-CARNITINE FOR THE PREPARATION OF A MEDICAMENT IN THE FORM OF EYE-DROPS FOR TREATING CORNEAL DISEASES

(75) Inventors: Aleardo Koverech, Rome (IT); Nicola Pescosolido, Rome (IT)

(73) Assignee: SIGMA-TAU Industrie Farmaceutiche Riunite S.p.A., Rome (IT)

( * ) Notice: Subject to any disclaimer, the term of this patent is extended or adjusted under 35 U.S.C. 154(b) by 71 days.

(21) Appl. No.: 12/515,142

(22) PCT Filed: Nov. 21, 2007

(86) PCT No.: PCT/EP2007/062610
§ 371 (c)(1),
(2), (4) Date: Oct. 7, 2009

(87) PCT Pub. No.: WO2008/071524
PCT Pub. Date: Jun. 19, 2008

(65) Prior Publication Data
US 2010/0068300 A1    Mar. 18, 2010

(30) Foreign Application Priority Data

Dec. 11, 2006  (EP) .................................. 06125770

(51) Int. Cl.
*A61K 31/197* (2006.01)
*A61K 31/221* (2006.01)
(52) U.S. Cl. ........................................ 514/547; 514/516
(58) Field of Classification Search .................. 514/516, 514/547
See application file for complete search history.

(56) References Cited

U.S. PATENT DOCUMENTS

| 2002/0017305 A1 | 2/2002 | Bagrov et al. |
| 2006/0106104 A1 | 5/2006 | Vehige et al. |
| 2007/0265338 A1 | 11/2007 | Koverech et al. |

FOREIGN PATENT DOCUMENTS

WO   2006044155 A   4/2006

*Primary Examiner* — Zohreh Fay
(74) *Attorney, Agent, or Firm* — Lucas & Mercanti, LLP

(57) ABSTRACT

Use of L-carnitine or a pharmaceutically acceptable salt thereof, for the preparation of an ophthalmic physiological supplement or medicament in the form of eye-drops, for the treatment of corneal oedema.

3 Claims, No Drawings

USE OF L-CARNITINE FOR THE PREPARATION OF A MEDICAMENT IN THE FORM OF EYE-DROPS FOR TREATING CORNEAL DISEASES

This application is a 371 of PCT/EP2007/062610 filed on Nov. 21, 2007, which claims the benefit of European Patent Application No. 06125770.5 filed on Dec. 11, 2006, the contents of each of which are incorporated herein by reference.

The present invention relates to a physiological supplement or medicament, in the form of eye-drops, useful for the treatment of corneal diseases.

In particular, the present invention relates to a physiological supplement or medicament for ophthalmic use, in the form of eye-drops, comprising as the active ingredient L-carnitine, or a pharmaceutically acceptable salt thereof, in combination with humidifying agents such as sodium hyaluronate; antioxidants such as vitamin E; inorganic and organic elements such as zinc, manganese, sodium, potassium and taurine; useful for preparing a physiological supplement or medicament for the treatment of corneal oedema.

The cornea is the transparent, dome-shaped window covering the front of the eye. It is a powerful refracting surface, providing ⅔ of the eye's focusing power. Like the crystal on a watch, it gives us a clear window to look through.

The cornea is extremely sensitive, there are more nerve endings in the cornea than anywhere else in the body.

The adult cornea is only about ½ millimeter thick and is arranged in three main regions, or layers:

Epithelium: it functions primarily to block the passage of foreign material such as dust or water into the eye, and other layers of the cornea, and provide a smooth surface that absorbs oxygen and other needed cell nutrients that are contained in tears. This layer, which is about five cells deep, is filled with thousands of tiny nerve endings that make the cornea extremely sensitive to pain when rubbed or scratched.

Stroma: is located behind the epithelium, the stroma comprises about 90 percent of the cornea. It consists primarily of water and layered protein fibers that give the cornea its strength, elasticity, and form; and cells that nourish it. The unique shape, arrangement, and spacing of the protein fibers are essential in producing the cornea's light-conducting transparency.

Endothelium: this single layer of cells is located between the stroma and the aqueous humor. Because the stroma tends to absorb water, the endothelium's primary task is to pump excess water out of the stroma. Without this pumping action, the stroma would swell with water, become hazy, and ultimately opaque.

Oedema, or swelling, of the cornea occurs when the cornea is unable to keep itself clear and fluid begins to accumulate within it. The inside lining of the cornea is responsible for keeping it clear, and if this layer is damaged symptoms of corneal oedema may occur.

Causes of corneal oedema include: (a) disorders of the inside layer of the cornea such as Fuchs' endothelial dystrophy; eye surgery such as cataract surgery; eye trauma; acute glaucoma with very high eye pressure; or (b) neurotrophic keratopathy caused by: infections due to, for example Herpes virus or mycobacterium leprae; lesions of cranial nerve V due to traumatic lesions, chirurgic lesions, tumor, aneurism, or genetic causes; metabolic, due to diabetes or vitamin A deficiency; iatrogenic, due to ocular and laser chirurgy, contact lens, radio therapy; toxic, due abuse of topic anaesthetic, chronic use of hypotonic eye drops, non steroideal antiinflammatory drugs, eydrops preservatives such as benzalconium chloride; exposure to chemical or physical agents such as smokes, acid, alkaly, attinic keratitis; chronic inflammation due to blepharitis, springs keratoconjunctivitis, giantopapillar keratoconjunctivitis, athopic keratoconjunctivitis; alteration of the eyelid position such as thyroideal ophthalmopathy, Entopion and Ectropion, paretic lagophthalmo.

Treatment of corneal oedema depends on its cause. Mild oedema can be treated with hypertonic eye drops and ointment. This draws fluid out of the cornea and into the tears, and helps to clear the cornea. More severe oedema, especially with blister (bullae) formation, may require corneal transplant to correct.

The development of corneal oedema during hydrogel contact lens wear is well documented; however, the magnitude of lens-induced swelling cannot be completely explained in terms of a response to hypoxia.

Sodium hyaluronate is a very well known compound used to protect corneal epithelial cells, especially in patients with dry eye syndrome or with Sjögren's syndrome. The action of sodium hyaluronate is due not only to its protective role of a mechanical type exerted on the epithelial cells as a result of its viscoelasticity, in situations of reduced tear production, but also to the positive effects of its particular biological function on corneal epithelial cells by stimulating their migration (*Exp. Eye Res.,* 1991; 53:753-758).

Taurine (or 2-aminoethanesulphonic acid) is considered an amino acid, even though it does not possess the characteristic carboxyl group (COOH) but the $SO_3H$ group. Taurine is only present in the animal realm, whereas vegetable foods do not possess this amino acid.

Vitamin E is the main antioxidant of the cell membranes, and is found in the human body in 4 forms consisting of α-tocopherol, β-tocopherol, γ-tocopherol and δ-tocopherol. Of these the a form is the most frequent in the retina and in plasma and is the one with the greatest antioxidant and free radical scavenging activity.

The use of inorganic elements is well known in the medical field, and a number of these are essential for the stability of the tear film (Pescosolido 2000).

Previous uses of L-carnitine in ophthalmological field is already known.

In Eur. J. Ophthalmol. 2003 Jan.-Feb.; 13(1):80-5 is reported that L-carnitine is useful for preventing retinal injury followed by ischemia-reperfusion.

In J. Ocul. Pharmacol. 1994 Winter; 10(4):643-51, is reported that free carnitine and acid soluble acylcarnitines are present in various tissues of the rabbit eye and play an important role in those tissues of the eye where cells of a muscular nature are present and may represent, after esterification, an important energy reserve.

In Res 1992; 18(8):355-365 the use of L-carnitine in the cardiological field is described.

None of the above-cited patents or publications describes or suggests the use of L-carnitine for the treatment of corneal oedema.

In the medical field there is still a strongly perceived need for the availability of therapeutic agents or physiological supplement useful for the treatment of the above-mentioned corneal diseases.

It has now been found that a physiological supplement or medicament for ophthalmic use, in the form of eye-drops, comprising as the active ingredient L-carnitine, or a pharmaceutically acceptable salt thereof, in combination with humidifying agents such as sodium hyaluronate; antioxidants such as vitamin E; inorganic and organic elements such as zinc, manganese, sodium, potassium and taurine; and optionally one or more ophthalmologically acceptable excipient and/or diluent is useful for preparing a medicament or a physiological supplement for the treatment of corneal oedema.

What is meant by pharmaceutically acceptable salt of L-carnitine is any salt of the latter with an acid that does not give rise to toxic or side effects.

These acids are well known to pharmacologists and to experts in pharmacy. Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

What is meant by pharmaceutically acceptable salt of L-carnitine is also a salt approved by the FDA and listed in the publication *Int. J. of Pharm.* 33 (1986), 201-217, which is incorporated herein by way of a reference.

A further object of the present invention is a physiological supplement or medicament for ophthalmic use, in the form of eye-drops, comprising as active ingredients:

L-carnitine at a dose of 5-15%; preferred dose is 10%;
taurine at a dose of 0.05-4%, preferred dose is 2%;
sodium hyaluronate at a dose of 0.05-1.5%, preferred dose is 0.2%;
vitamin E at a dose of 0.05-1.0%, preferred dose is 0.2%;
manganese at a dose of 0.01-0.1 mg/L, preferred dose is 0.051 mg/L;
zinc at a dose of 0.5-1.5 mg/mL, preferred dose is 1.02 mg/mL;
sodium at dose of 5-5000 mg/L, preferred dose is 30 mg/L;
potassium at a dose of 1-1000 mg/L, preferred dose is 9 mg/L.

It is a further object of the present invention the use of the eye drops of the invention, for the preparation of a physiological supplement or a medicament for the prevention or treatment of corneal oedema caused by: (a) disorders of the inside layer of the cornea due to Fuchs' endothelial dystrophy; eye surgery such as cataract surgery; eye trauma; acute glaucoma with very high eye pressure; or (b) neurotrophic keratopathy caused by: infections due to, for example Herpes virus or mycobacterium leprae; lesions of cranial nerve V due to traumatic lesions, chirurgic lesions, tumor, aneurism, or genetic causes; metabolic, due to diabetes or vitamin A deficiency; iatrogenic, due to ocular and laser chirurgy, contact lens, radio therapy; toxic, due abuse of topic anaesthetic, chronic use of hypotonic eye drops, non steroideal antiinflammatory drugs, eydrops preservatives such as benzalconium chloride; exposure to chemical or physical agents such as smokes, acid, alkaly, attinic keratitis; chronic inflammation due to blepharitis, springs keratoconjunctivitis, giantopapillar keratoconjunctivitis, athopic keratoconjunctivitis; alteration of the eyelid position such as thyroideal ophthalmopathy, Entopion and Ectropion, paretic lagophthalmo.

The eye-drops according to the present invention may additionally contain further antioxidants such as vitamin C, vitamin A; Borage oil; epithelialising and anti-angiogenic agents; citicholine; humidifying agents; inorganic elements; regulator of the cellular osmolarity; antibiotics; antiviral agents; antifungal agents; and/or one or more alkanoyl L-carnitines selected from the group consisting of acetyl, propionyl, valeryl, isovaleryl, butyryl and isobutyryl L-carnitine, or a pharmaceutically acceptable salt thereof.

The following examples illustrate the invention.

EXAMPLE 1

15 Patients with corneal oedema (due to cornea guttata) were treated for a month with the eye drops of the invention.

The patients were monitored (every week) using the following examinations, before and after the administration of the eye drops of the invention:

Electronic pachymetry
Confocal microscopy
Contrast sensitivity

Using pachymetry the central and paracentral thickness of the cornea was measured in microns. The five corneal layers were examined by confocal microscopy, evaluating the number of endothelial cells, their polymegathism and pleomorphism. The stromal cells and epithelial cells were also examined using the same procedure. Finally, as a functional examination, the contrast sensitivity curve was plotted at the different cycles per degree from 0.5 to 12.

Results

Using pachymetry, the analysis of the values obtained before and after the administration of the eye drops of the invention revealed a reduction of approximately 25% in the thickness of the cornea both in the central and the paracentral zone, which lasted for approximately 4-6 hours after administration.

The evaluations performed using confocal microscopy revealed better definition of the stromal cell margins, a clear sign that there had been a significant reduction of the oedema. Similarly this reduction was also apparent in the epithelial cells.

The functional examination confirmed the morphological data, finding a significant increase in the values of the sensitivity curve which restored the physiological values.

These therapeutical effect was confirmed/maintained during following periodic medical and instrumental examinations.

L-carnitine is a known compounds which preparation is described in U.S. Pat. No. 4,254,053.

The physiological supplement or medicament according to the present invention may be bought with or without medical prescription.

The physiological supplement or medicament according to the present invention is composed of active ingredients which are familiar to operators in the medical field and already in use in clinical practice, and their pharmacotoxicological profiles are known.

Their procurement therefore is very easy, inasmuch as these are products which have been on the market now for a long time and are of a grade suitable for human or animal administration.

In the following are reported non limiting examples of composition according to the present invention.

Eye-Drops (about 1200 mOsm/L)

| | |
|---|---|
| L-carnitine | 10% |
| taurine | 2% |
| sodium jaluronate | 0.2% |
| vitamin E | 0.2% |
| zinc | 1.02 mg/L |
| manganese | 0.051 mg/L |
| sodium | 30 mg/L |
| potassium | 9 mg/L |

-continued

| | |
|---|---|
| Sodium mertiolate | 0.02 mg/mL |
| Demineralized water Volume | 5 mL/vials. |

The invention claimed is:

1. A physiological supplement or medicament for ophthalmic use, in the form of eye-drops, comprising:

| | |
|---|---|
| L-carnitine or a salt thereof | 5-15%; |
| Taurine | 0.05-4%; |
| Sodium hyaluronate | 0.05-1.5%; |
| Vitamin E | 0.05-1%; |
| Zinc | 0.5-1.5%; |
| Manganese | 0.01-0.1 mg/L; |
| Sodium | 5-5000 mg/L; and |
| Potassium | 1-1000 mg/L. |

2. The salt of L-carnitine of claim 1, selected from the group consisting of: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

3. The eye-drops of claim 1, further comprising one or more diluents and/or excipients ophtalmologically acceptable.

* * * * *